United States Patent
Rudnic et al.

(10) Patent No.: US 6,610,328 B2
(45) Date of Patent: *Aug. 26, 2003

(54) AMOXICILLIN-CLARITHROMYCIN ANTIBIOTIC COMPOSITION

(75) Inventors: Edward M. Rudnic, N. Potomac, MD (US); James D. Isbister, Potomac, MD (US); Donald J. Treacy, Jr., Arnold, MD (US); Sandra E. Wassink, Frederick, MD (US)

(73) Assignee: Advancis Pharmaceutical Corp., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/093,321

(22) Filed: Mar. 7, 2002

(65) Prior Publication Data

US 2003/0077323 A1 Apr. 24, 2003

Related U.S. Application Data

(63) Continuation-in-part of application No. 09/791,983, filed on Feb. 23, 2000.
(60) Provisional application No. 60/184,545, filed on Feb. 24, 2000.

(51) Int. Cl.$^7$ .............................. A61K 9/16; A61K 9/20; A61K 9/22; A61K 9/26; A61K 9/48
(52) U.S. Cl. ........................ 424/468; 424/451; 424/452; 424/457; 424/458; 424/464; 424/465; 424/469; 424/489; 424/490; 424/493; 424/494
(58) Field of Search ................................ 424/451, 452, 424/457, 458, 464, 465, 468, 469, 489, 490, 493, 494

(56) References Cited

U.S. PATENT DOCUMENTS

| | | | |
|---|---|---|---|
| 4,435,173 A | 3/1984 | Siposs et al. | 609/155 |
| 4,616,008 A | 10/1986 | Hirai et al. | 514/200 |
| 4,794,001 A * | 12/1988 | Mehta et al. | 424/458 |
| 4,831,025 A | 5/1989 | Godtfredsen et al. | 514/195 |
| 4,904,476 A | 2/1990 | Mehta et al. | 424/456 |
| 4,915,953 A | 4/1990 | Jordan et al. | 424/473 |
| 4,971,805 A | 11/1990 | Kitanishi et al. | 424/494 |
| 5,011,692 A * | 4/1991 | Fujioka et al. | 424/426 |
| 5,110,597 A | 5/1992 | Wong et al. | 424/438 |
| 5,213,808 A | 5/1993 | Bar-Shalom et al. | 424/473 |
| 5,229,131 A | 7/1993 | Amidon et al. | 424/451 |
| 5,395,626 A | 3/1995 | Kotwal et al. | 424/472 |
| 5,401,512 A | 3/1995 | Rhodes et al. | 424/458 |
| 5,414,014 A | 5/1995 | Schneider et al. | 514/535 |
| 5,445,829 A | 8/1995 | Paradissis et al. | 424/480 |
| 5,462,747 A | 10/1995 | Radebaugh et al. | 424/465 |
| 5,472,708 A | 12/1995 | Chen | 424/451 |
| 5,508,040 A | 4/1996 | Chen | 424/451 |
| 5,567,441 A | 10/1996 | Chen | 424/494 |
| 5,672,359 A | 9/1997 | Digenis et al. | 424/463 |
| 5,719,132 A | 2/1998 | Lin et al. | 514/50 |
| 5,827,531 A | 10/1998 | Morrison et al. | 424/450 |
| 5,840,329 A | 11/1998 | Bai | 424/458 |
| 5,877,243 A | 3/1999 | Sarangapani | 524/139 |
| 5,910,322 A | 6/1999 | Rivett et al. | 424/484 |
| 6,027,748 A | 2/2000 | Conte et al. | 424/458 |
| 6,132,771 A | 10/2000 | Depui et al. | 424/468 |
| 6,294,199 B1 | 9/2001 | Conley et al. | 424/468 |
| 6,358,525 B1 | 3/2002 | Guo et al. | 424/464 |
| 2001/0046984 A1 | 11/2001 | Rudnic et al. | 514/210.09 |
| 2001/0048944 A1 | 12/2001 | Rudnic et al. | 424/468 |
| 2002/0004070 A1 | 1/2002 | Rudnic et al. | 424/468 |
| 2002/0004499 A1 | 1/2002 | Rudnic et al. | 514/192 |

FOREIGN PATENT DOCUMENTS

| | | |
|---|---|---|
| WO | WO 94/27557 | 12/1994 |
| WO | WO 95/20946 | 8/1995 |
| WO | WO 96/04908 | 2/1996 |
| WO | WO 98/22091 | 5/1998 |

OTHER PUBLICATIONS

Erah et al.; "The stability of amoxycillin, clarithromycin and metronidazole in gastric juice: relevance to the treatment of *Helicobacter pylori* infection"; J Antimicrob Chemother Jan. 1997; 39(1): 5–12.*

* cited by examiner

Primary Examiner—Thurman K. Page
Assistant Examiner—S. Tran
(74) Attorney, Agent, or Firm—Elliot M. Olstein; Raymond E. Stauffer

(57) ABSTRACT

An antibiotic product for delivering at least Amoxicillin or Clarithromycin that is comprised of three dosage forms with different release profiles with each of Amoxicillin and Clarithromycin being present in at least one of the dosage forms.

66 Claims, No Drawings

AMOXICILLIN-CLARITHROMYCIN ANTIBIOTIC COMPOSITION

This application is a continuation-in-part of application Ser. No. 09/791,983, filed Feb. 23, 2000, which claims the priority of U.S. Provisional Application Ser. No. 60/184,545 filed on Feb. 24, 2000, the disclosure of which is hereby incorporated by reference in its entirety.

This invention relates to antibiotic compositions and the use thereof. More particularly, this invention relates to a composition for the delivery of two or more antibiotics, and the use thereof.

In many cases, it is desirable to employ two different antibiotics in the treatment of a bacterial infection, in that such antibiotics may have complementary mechanisms of action that facilitate treatment of the bacterial infection.

The present invention is directed to a new and improved composition that delivers two or more antibiotics, and the use thereof, with the two antibiotics being Amoxicillin and Clarithromycin.

In accordance with an aspect of the present invention, there is provided an antibiotic product for delivering at least two different antibiotics that is comprised of at least three dosage forms each comprised of at least one antibiotic and a pharmaceutically acceptable carrier, with one of the dosage forms including at least one of the at least two antibiotics and at least one dosage form including at least a second antibiotic of the at least two antibiotics, wherein one of the antibiotics is Amoxicillin and the other antibiotic is Clarithromycin.

Thus, for example, each of the dosage forms may include two or more antibiotics, or one or two of the dosage forms may include only one of the two or more antibiotics and each of the remaining dosage forms may include only one or more of the different antibiotics or two or more of the antibiotics. Thus, in accordance with this aspect of the invention, there is an antibiotic product for delivering at least two different antibiotics wherein the product includes at least three dosage forms wherein each of the at least two antibiotics is present in at least one of the three dosage forms. In each case, one of the antibiotics is Amoxicillin and the other of the antibiotics is Clarithromycin.

In a preferred embodiment each of the dosage forms has a different release profile, with one of the dosage forms being an immediate release dosage form.

In another aspect, the present invention is directed to treating a bacterial infection by administering to a host in need thereof an antibiotic product as hereinabove and hereinafter described.

Thus, in accordance with an aspect of the present invention, there is provided a single or unitary antibiotic product that has contained therein at least three antibiotic dosage forms, each of which has a different release profile, whereby the antibiotic contained in each of the at least three dosage forms is released at different times, and wherein at least one of the dosage forms includes at least Amoxicillin and at least one of the dosage forms includes at least Clarithromycin. One or more of the dosage forms may include both Amoxicillin and Clarithromycin.

In accordance with a further aspect of the invention, the antibiotic product may be comprised of at least four different dosage forms, each of which starts to release the antibiotic contained therein at different times after administration of the antibiotic product.

The antibiotic product generally does not include more than five dosage forms with different release times.

In accordance with a preferred embodiment, the antibiotic product has an overall release profile such that when administered the maximum serum concentration of the total antibiotic released from the product is reached in less than twelve hours, preferably in less than eleven hours. In an embodiment, the maximum serum concentration of the total antibiotic released from the antibiotic product is achieved no earlier than four hours after administration.

In accordance with one preferred embodiment of the invention, one of the at least three dosage forms is an immediate release dosage form whereby initiation of release of antibiotic therefrom is not substantially delayed after administration of the antibiotic product. The second and third of the at least three dosage forms is a delayed dosage form (which may be a pH sensitive or a non-pH sensitive delayed dosage form, depending on the type of antibiotic product), whereby antibiotic released therefrom is delayed until after initiation of release of antibiotic from the immediate release dosage form. More particularly, antibiotic release from the second of the at least two dosage forms achieves a $C_{max}$ (maximum serum concentration in the serum) at a time after antibiotic released from the first of the at least three dosage forms achieves a $C_{max}$ in the serum, and antibiotic released from the third dosage form achieves a $C_{max}$ in the serum after the $C_{max}$ of antibiotic released from the second dosage form.

In one embodiment, the second of the at least two dosage forms initiates release of antibiotic contained therein at least one hour after the first dosage form, with the initiation of the release therefrom generally occurring no more than six hours after initiation of release of antibiotic from the first dosage form of the at least three dosage forms.

In general, the immediate release dosage form produces a $C_{max}$ for antibiotic released therefrom within from about 0.5 to about 2 hours, with the second dosage form of the at least three dosage forms producing a $C_{max}$ for antibiotic released therefrom in no more than about four hours. In general, the $C_{max}$ for such second dosage form is achieved no earlier than two hours after administration of the antibiotic product; however, it is possible within the scope of the invention to achieve $C_{max}$ in a shorter period of time.

As hereinabove indicated, the antibiotic product may contain at least three or at least four or more different dosage forms. For example, the antibiotic released from the third dosage form reaches a $C_{max}$ at a time later than the $C_{max}$ is achieved for antibiotic released from each of the first and second dosage forms. In a preferred embodiment, release of antibiotic from the third dosage form is started after initiation of release of antibiotic from both the first dosage form and the second dosage form. In one embodiment, $C_{max}$ for antibiotic release from the third dosage form is achieved within eight hours.

In another embodiment, the antibiotic product contains at least four dosage forms, with each of the at least four dosage forms having different release profiles, whereby antibiotic released from each of the at least four different dosage forms achieves a $C_{max}$ at a different time.

As hereinabove indicated, in a preferred embodiment, irrespective of whether the antibiotic contains at least three or at least four different dosage forms each with a different release profile, $C_{max}$ for all the antibiotic released from the antibiotic product is achieved in less than twelve hours, and more generally is achieved in less than eleven hours.

In a preferred embodiment, the antibiotic product is a once a day product, whereby after administration of the antibiotic product, no further product is administered during the day; i.e., the preferred regimen is that the product is administered only once over a twenty-four hour period. Thus, in accordance with the present invention, there is a single administration of an antibiotic product with the antibiotic being released in a manner such that overall antibiotic release is effected with different release profiles in a manner such that the overall $C_{max}$ for the antibiotic product is reached in less than twelve hours. The term single administration means that the total antibiotic administered over a twenty-four hour period is administered at the same time, which can be a single tablet or capsule or two or more thereof, provided that they are administered at essentially the same time.

Thus in accordance with an aspect of the invention, there is provided a single dosage antibiotic product comprised of at least three antibiotic dosage forms each having a different release profile with each of the dosage forms including at least one of Amoxicillin or Clarithromycin and at least one of the three dosage forms including at least Amoxicillin and at least one of the dosage forms including at least Clarithromycin. Each of the dosage forms of antibiotic in a pharmaceutically acceptable carrier may have one or more antibiotics.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antibiotic may occur. Such "leakage" is not "release" as used herein.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, antibiotic release from such fourth dosage form may be initiated prior to or after release from the second or third dosage form.

In accordance with an aspect of the present invention, there is provided an antibiotic composition that is a mixture of antibiotic compositions or dosage forms wherein said composition contains a first composition or dosage form comprising a first antibiotic and a pharmaceutically acceptable carrier; a second composition or dosage form comprising the first antibiotic and a pharmaceutically acceptable carrier; a third composition or dosage form comprising a second antibiotic different from the first antibiotic and a pharmaceutically acceptable carrier; and a fourth composition or dosage form comprising the second antibiotic and a pharmaceutically acceptable carrier; wherein the second and third compositions each have a release profile that provides a maximum serum concentration of the first antibiotic released from the second composition and a maximum serum concentration for the second antibiotic released from the third composition at a time after the first antibiotic released from the first composition reaches a maximum serum concentration, and wherein the fourth composition has a release profile that provides for a maximum serum concentration of the second antibiotic released from the fourth composition at a time after the antibiotics released from the second and third compositions reach a maximum serum concentration. The first antibiotic is one of Amoxicillin or Clarithromycin and the second antibiotic is the other of Amoxicillin or Clarithromycin.

In one embodiment, the release profiles of the second and third composition are such that the maximum serum concentration of the first antibiotic released from the second composition, and the maximum serum concentration of the second antibiotic released from the third composition are reached at approximately the same time, or where the first antibiotic reaches a maximum serum concentration before or after the second antibiotic reaches a maximum serum concentration.

In effect, in accordance with a preferred embodiment of the present invention, there is provided a first pulse in which a first antibiotic reaches a maximum serum concentration, a second pulse wherein a further dosage of the first antibiotic, and an initial dosage of the second antibiotic reach a maximum serum concentration at a time after the first pulse of the first antibiotic reaches a maximum serum concentration, and a third pulse wherein an additional dosage of the second antibiotic reaches a maximum serum concentration at a time after the maximum serum concentration is reached for each of the first and second antibiotic dosages provided in the second pulse.

In a preferred embodiment of the present invention, the first dosage of the first antibiotic achieves a maximum serum concentration within four hours after administration of the antibiotic composition; the second dosage of the first antibiotic and the first dosage of the second antibiotic each reach a maximum serum concentration within four to eight hours after administration of the antibiotic composition; and the second dosage of the second antibiotic reaches a maximum serum concentration within twelve hours after administration of the antibiotic composition.

Thus, in accordance with an aspect of the present invention, there is provided an antibiotic composition that includes four different dosage forms, with the first dosage form providing an initial dosage of a first antibiotic, the second dosage form providing a further dosage of the first antibiotic; the third dosage form providing an initial dosage of a second antibiotic; and the fourth dosage form providing an additional dosage of the second antibiotic, wherein the antibiotics released from the second and third dosage forms reach a maximum serum concentration at a time after the antibiotic released from the first dosage form reaches a maximum serum concentration, and the antibiotic released from the fourth dosage form reaching a maximum serum concentration at a time after the times at which the antibiotics released from each of the first, second, and third dosage forms reach a maximum serum concentration.

In one embodiment of the invention, the first dosage form provides for immediate release, the second and third dosage forms provide for a delayed release (pH or non pH dependent, with the second dosage form preferably being a pH dependent release), and the fourth dosage form provides for pH dependent or non pH dependent release preferably non pH dependent release.

In formulating the antibiotic composition of the present invention, which contains four different dosage forms, as hereinabove described, the first dosage form generally contains from about 30 percent to about 80 percent of the first antibiotic; the second dosage form contains from about 30 percent to about 80 percent of the first antibiotic; the third dosage form contains from about 30 percent to about 80 percent of the second antibiotic, and the fourth antibiotic dosage form contains from about 30 percent to about 80 percent of the second antibiotic. In formulating a composition comprised of such four dosage forms or units, each unit or dosage form is present in an amount of at least 20 percent by weight, with each dosage form or unit being present in the overall composition in an amount that generally does not exceed 60 percent by weight.

Each of the first and second dosage forms include from 20% to 80% of the total dosage of the first antibiotic to be provided by the composition, and each of the first and second dosage forms may include the same or different dosages of the first antibiotic.

Each of the third and fourth dosage forms include from 20% to 80% of the total dosage of the second antibiotic to be delivered by the composition, and each of the third and fourth units may have the same or different dosages of the antibiotic.

In formulating an antibiotic product in accordance with the invention, in one embodiment, the immediate release dosage form of the product generally provides from about 20% to about 50% of the total dosage of antibiotic to be delivered by the product, with such immediate release dosage form generally providing at least 25% of the total dosage of the antibiotic to be delivered by the product. In many cases, the immediate release dosage form provides from about 20% to about 30% of the total dosage of antibiotic to be delivered by the product; however, in some cases it may be desirable to have the immediate release dosage form provide for about 45% to about 50% of the total dosage of antibiotic to be delivered by the product.

The remaining dosage forms deliver the remainder of the antibiotic. If more than one delayed release dosage form is used, in one embodiment, each of the delayed release dosage forms may provide about equal amounts of antibiotic; however, they may also be formulated so as to provide different amounts.

In one embodiment, where the composition contains one immediate release component and two delayed release components, the immediate release component provides from 20% to 35% (preferably 20% to 30%), by weight, of the total antibiotic; where there is three delayed release components, the immediate release component provides from 15% to 30%, by weight, of the total antibiotic; and where there are four delayed release components, the immediate release component provides from 10% to 25%, by weight, of the total antibiotic.

With respect to the delayed release components, where there are two delayed release components, the first delayed release component (the one released earlier in time) provides from 30% to 60%, by weight, of the total antibiotic provided by the two delayed release components with the second delayed release component providing the remainder of the antibiotic.

Where there are three delayed release components, the earliest released component provides 20% to 35% by weight of the total antibiotic provided by the three delayed release components, the next in time delayed release component provides from 20% to 40%, by weight, of the antibiotic provided by the three delayed release components and the last in time providing the remainder of the antibiotic provided by the three delayed release components.

When there are four delayed release components, the earliest delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total antibiotic provided by the four delayed release components.

The overall composition includes each of the antibiotics in a therapeutically effective amount. The specific amount(s) is dependant on the antibiotic used, the disease or infection to be treated, and the number of times of day that the composition is to be administered.

The antibiotic composition of the present invention may be administered for example, by any one of the following routes of administration: sublingual, transmucosal, transdermal, parenteral, oral, preferably by oral administration.

The antibiotic product of the present invention, as hereinabove described, may be formulated for administration by a variety of routes of administration. For example, the antibiotic product may be formulated in a way that is suitable for topical administration; administration in the eye or the ear; rectal or vaginal administration; as nose drops; by inhalation; as an injectable; or for oral administration. In a preferred embodiment, the antibiotic product is formulated in a manner such that it is suitable for oral administration.

For example, in formulating the antibiotic product for topical administration, such as by application to the skin, the at least two different dosage forms, each of which contains an antibiotic, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an antibiotic product in the form of a patch, which includes antibiotic dosage forms having different release profiles, as hereinabove described.

In addition, the antibiotic product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the antibiotic product with at least three different dosage forms with different release profiles may be formulated for rectal or vaginal administration, as known in the art. This may take the form of a cream or emulsion, or other dissolvable dosage form similar to those used for topical administration.

As a further embodiment, the antibiotic product may be formulated for use in inhalation therapy by coating the particles and micronizing the particles for inhalation.

In a preferred embodiment, the antibiotic product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antibiotic product. Thus, for example, antibiotic products may include a first dosage form in the form of a tablet that is an immediate release tablet, and may also include two or more additional tablets, each of which provides for a delayed release of the antibiotic, as hereinabove described, whereby the $C_{max}$ of the antibiotic released from each of the tablets is reached at different times, with the $C_{max}$ of the total antibiotic released from the antibiotic product being achieved in less than twelve hours.

The formulation of an antibiotic product including at least three dosage forms with different release profiles for different routes of administration is deemed to be within the skill of the art from the teachings herein. As known in the art, with respect to delayed release, the time of release can be controlled by the concentration of antibiotics in the coating and/or the thickness of the coating.

As hereabove indicated, the first and second antibiotics employed in the antibiotic composition may be a wide variety of products. In one embodiment, the combination of first and second antibiotics that are used in the composition may be, for example, a penicillin and an aminoglycoside, such as gentamycin, tobramicin, amikacin or vancomycin. Another antibiotic composition that may be employed is a combination of a sulfonamide, such as sulfamethoxasol, which would be combined with trimethoporim. In a preferred embodiment, the first and second, antibiotics are different antibiotics and each is from a different class of antibiotic.

The Immediate Release Component.

The immediate release portion of this system can be a mixture of ingredients that breaks down quickly after administration to release the antibiotic. This can take the form of either a discrete pellet or granule that is mixed in with, or compressed with, the other three components.

The materials to be added to the antibiotics for the immediate release component can be, but are not limited to, microcrystalline cellulose, corn starch, pregelatinized starch, potato starch, rice starch, sodium carboxymethyl starch, hydroxypropylcellulose, ydroxypropylmethylcellulose, hydroxyethylcellulose, ethylcellulose, chitosan, hydroxychitosan, hydroxymethylatedchito san, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000–10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The Enteric Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

The invention will be further described with respect to the following examples; however the scope of the invention is not limited thereby. All percentages stated in this specification are by weight, unless otherwise specified.

EXAMPLES

| Ingredient | Conc. (% W/W) | |
|---|---|---|
| Immediate Release Component | | |
| Example 1: | | |
| Amoxicillin | 65% | (W/W) |
| Microcrystalline cellulose | 20 | |
| Povidone | 10 | |
| Croscarmellose sodium | 5 | |
| Example 2: | | |
| Amoxicillin | 55% | (W/W) |
| Microcrystalline cellulose | 25 | |
| Povidone | 10 | |
| Croscarmellose sodium | 10 | |
| Example 3: | | |
| Amoxicillin | 65% | (W/W) |
| Microcrystalline cellulose | 20 | |
| Hydroxypropylcellulose | 10 | |
| Croscarmellose sodium | 5 | |
| Example 4: | | |
| Amoxicillin | 75% | (W/W) |
| Polyethylene glycol 4000 | 10 | |
| Polyethylene glycol 2000 | 10 | |
| Hydroxypropylcellulose | 5 | |
| Example 5: | | |
| Amoxicillin | 75% | (W/W) |
| Polyethylene glycol 8000 | 20 | |
| Polyvinylpyrrolidone | 5 | |
| Example 6: | | |
| Clarithromycin | 65% | (W/W) |
| Microcrystalline cellulose | 20 | |
| Hydroxypropylcellulose | 10 | |
| Croscarmellose sodium | 5 | |
| Example 7: | | |
| Clarithromycin | 75% | (W/W) |
| Microcrystalline cellulose | 15 | |
| Hydroxypropylcellulose | 5 | |
| Croscarmellose sodium | 5 | |
| Example 8: | | |
| Clarithromycin | 75% | (W/W) |
| Polyethylene glycol 4000 | 10 | |
| Polyethylene glycol 2000 | 10 | |
| Hydroxypropylcellulose | 5 | |
| Example 9: | | |
| Clarithromycin | 75% | (W/W) |
| Polyethylene glycol 8000 | 20 | |
| Polyvinylpyrrolidone | 5 | |
| Example 10: | | |
| Ciprofoxacin | 65% | (W/W) |
| Microcrystalline cellulose | 20 | |
| Hydroxypropylcellulose | 10 | |
| Croscarmellose sodium | 5 | |

| Ingredient | Conc. (% W/W) | |
|---|---|---|
| *Example 11:* | | |
| Ciprofoxacin | 75% | (W/W) |
| Microcrystalline cellulose | 15 | |
| Hydroxypropylcellulose | 5 | |
| Croscarmellose sodium | 5 | |
| *Example 12:* | | |
| Ciprofoxacin | 75% | (W/W) |
| Polyethylene glycol 4000 | 10 | |
| Polytheylene glycol 2000 | 10 | |
| Hydroxypropylcellulose | 5 | |
| *Example 13:* | | |
| Cirpofoxacin | 75% | (W/W) |
| Polyethylene glycol 8000 | 20 | |
| Polyvinylpyrrolidone | 5 | |
| *Example 14:* | | |
| Ceftibuten | 75% | (W/W) |
| Polyethylene glycol 4000 | 10 | |
| Polyethylene glycol 2000 | 10 | |
| Hydroxypropylcellulose | 5 | |
| *Example 15:* | | |
| Ceftibuten | 75% | (W/W) |
| Polyethylene Glycol 4000 | 20 | |
| Polyvinylpyrrolidone | 5 | |
| Delayed Release Component (non-pH dependant) | | |
| *Example 16:* | | |
| Amoxicillin | 65% | (W/W) |
| Microcrystalline cellulose | 20 | |
| Polyox | 10 | |
| Croscarmellose sodium | 5 | |
| *Example 17:* | | |
| Amoxicillin | 55% | (W/W) |
| Microcrystalline cellulose | 25 | |
| Polyox | 10 | |
| Glyceryl monooleate | 10 | |
| *Example 18:* | | |
| Amoxicillin | 65% | (W/W) |
| Polyox | 20 | |
| Hydroxypropylcellulose | 10 | |
| Croscarmellose sodium | 5 | |
| *Example 19:* | | |
| Clarithromycin | 70% | (W/W) |
| Polyox | 20 | |
| Hydroxypropylcellulose | 5 | |
| Croscarmellose sodium | 5 | |
| *Example 20:* | | |
| Gentamicin | 20% | (W/W) |
| Sodium lauryl sulfate | 2 | |
| Sodium monoglycerides | 10 | |
| Sodium diglycerides | 20 | |
| Diethyleneglycolmethylether | 5 | |
| Microcrystalline cellulose | 43 | |
| *Example 21:* | | |
| Gentamicin | 10% | (W/W) |
| Glyvceryl behanate | 30 | |
| Pluronic | 10 | |
| Carbopol 94P | 30 | |
| Microcrystalline cellulose | 20 | |
| *Example 22:* | | |
| Gentamicin | 25% | (W/W) |
| Carbopol 94P | 35 | |
| Microcrystalline cellulose | 20 | |
| Vitamin E TPGS | 15 | |
| Sodium monoglycerate | 5 | |
| *Example 23:* | | |
| Amikacin | 25% | (W/W) |
| Carbopol 94P | 10 | |
| Sodium monoglycerate | 15 | |
| Sodium diglycerate | 15 | |
| Pluronic | 10 | |
| Lactose | 25 | |
| *Example 24:* | | |
| Gentamicin | 30% | (W/W) |
| Triacetin | 15 | |
| Capryol 90 | 5 | |
| Poloxamer Synperonic PE/F66 | 10 | |
| Cab-O-Sil | 5 | |
| Microcrystalline cellulose | 35 | |
| Enteric Release Component | | |
| *Example 25:* | | |
| Clarithromycin | 70% | (W/W) |
| Hydroxypropylcellulose pthalate | 15 | |
| Croscarmellose sodium | 10 | |
| *Example 26:* | | |
| Clarithromycin | 75% | (W/W) |
| Polyethylene glycol 2000 | 10 | |
| Eudragit E 30D | 15 | |
| *Example 27:* | | |
| Clarithromycin | 40% | (W/W) |
| Lactose | 50 | |
| Eudragit E 30D | 10 | |
| *Example 28:* | | |
| Ciprofoxacin | 65% | (W/W) |
| Microcrystalline Cellulose | 20 | |
| Eudragit E 30D | 10 | |
| *Example 29:* | | |
| Ciprofoxacin | 75% | (W/W) |
| Microcrystalline Cellulose | 15 | |
| Hydroxypropylcellulose pthalate | 10 | |
| *Example 30:* | | |
| Ciprofoxacin | 80% | (W/W) |
| Lactose | 10 | |
| Eudragit E 30D | 10 | |
| *Example 31:* | | |
| Ciprofoxacin | 70% | (W/W) |
| Polyethylene glycol 4000 | 20 | |
| Cellulose acetate pthalate | 10 | |
| *Example 32:* | | |
| Ceftibuten | 60% | (W/W) |
| Polyethylene glycol 2000 | 10 | |
| Lactose | 20 | |
| Eudragit E 30D | 10 | |
| *Example 33:* | | |
| Ceftibuten | 70% | (W/W) |
| Microcrystalline cellulose | 20 | |
| Cellulose acetate pthalate | 10 | |
| *Example 34:* | | |
| Amoxicillin | 65% | (W/W) |
| Microcrystalline cellulose | 20 | |
| Cellulose Acetate Pthalate | 15 | |
| *Example 35:* | | |
| Amoxicillin | 55% | (W/W) |
| Microcrystalline cellulose | 25 | |
| Cellulose Acetate Pthalate | 10 | |
| Hydroxypropylmethylcellulose | 10 | |

-continued

| Ingredient | Conc. (% W/W) | |
|---|---|---|
| Example 36: | | |
| Amoxicillin | 65% | (W/W) |
| Polyox | 20 | |
| Hydroxypropylcellulose pthalate | 10 | |
| Eudragit E30D | 5 | |
| Example 37: | | |
| Amoxicillin | 40% | (W/W) |
| Microcrystalline Cellulose | 40 | |
| Cellulose Acetate Pthalate | 10 | |
| Example 38: | | |
| Gentamicin | 20% | (W/W) |
| Sodium lauryl sulfate | 2 | |
| Sodium monoglycerides | 10 | |
| Sodium diglycerides | 20 | |
| Diethyleneglycolmethylether | 5 | |
| Microcrystalline cellulose | 30 | |
| Cellulose acetate pthalate | 13 | |
| Example 39: | | |
| Gentamicin | 10% | (W/W) |
| Glyceryl behanate | 30 | |
| Pluronic | 10 | |
| Carbopol 94P | 10 | |
| Microcrystalline cellulose | 20 | |
| Eudragit E30D | 20 | |
| Example 40: | | |
| Gentamicin | 25% | (W/W) |
| Carbopol 94P | 15 | |
| Microcrystalline cellulose | 20 | |
| Vitamin E TPGS | 15 | |
| Sodium Monoglycerate | 5 | |
| Eudragit E30D | 20 | |
| Example 41: | | |
| Amikacin | 25% | (W/W) |
| Carbopol 94P | 10 | |
| Sodium monoglycerate | 15 | |
| Sodium diglycerate | 15 | |
| Pluronic | 10 | |
| Lactose | 15 | |
| Cellulose acetate pthalate | 10 | |
| Example 42: | | |
| Gentamicin | 30% | (W/W) |
| Triacetin | 15 | |
| Capryol 90 | 5 | |
| Poloxamer SynperonicPE/F66 | 10 | |
| Cab-O-Sil | 5 | |
| Microcrystalline cellulose | 25 | |
| Eudragit E30D | 10 | |

Three Pulses

Example 43

1. Antibiotic Matrix Pellet Formulation and Preparation Procedure (Immediate Release)

A. Pellet Formulation

The composition of the antibiotic matrix pellets provided in Table 1.

TABLE 1

Composition of Antibiotic Pellets

| Component | Percentage (%) |
|---|---|
| Antibiotic | 50 |
| Avicel PH 101 | 20 |

TABLE 1-continued

Composition of Antibiotic Pellets

| Component | Percentage (%) |
|---|---|
| Lactose | 20 |
| PVP K29/32* | 10 |
| Purified Water | |
| Total | 100 |

*PVP K29/32 was added as a 20% w/w aqueous solution during wet massing.

B. Preparation Procedure for antibiotic Matrix Pellets 1.2.1 Blend metronidazole and Avicel® PH 101 using a Robot Coupe high shear granulator.

1.2.2 Add 20% Povidone K29/32 binder solution slowly into the powder blend under continuous mixing.

1.2.3 Extrude the wet mass using an LCI Bench Top Granulator. The diameter of the screen of the Bench Top Granulator was 1.0 mm.

1.2.4 Spheronize the extrudate using a Model SPH20 Caleva Spheronizer.

1.2.5 Dry the spheronized pellets at 50° C. overnight.

1.2.6 Pellets between 16 and 30 Mesh were collected for further processing.

The above procedure is used to make pellets of a first antibiotic and pellets of a second different antibiotic.

1.3 Preparation of an Eudragit® L 30 D-55 Aqueous Coating Dispersion

A. Dispersion Formulation

The composition of the aqueous Eudragit L30D-55 dispersion applied to the antibiotic matrix pellets is provided below in Table 2.

TABLE 2

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

B. Preparation Procedure for an Eudragit® L 30 D-55 Aqueous Dispersion 1.3.1 Suspend triethyl citrate and talc in deionized water.

1.3.2 The TEC/talc suspension is then homogenized using a PowerGen 700 high shear mixer.

1.3.3 Add the TEC/talc suspension slowly to the Eudragit® L 30 D-55 latex dispersion while stirring.

1.3.4 Allow the coating dispersion to stir for one hour prior to application onto the antibiotic matrix pellets.

1.4 Preparation of an Eudragit® S 100 Aqueous Coating Dispersion

A. Dispersion Formulation

The composition of the aqueous Eudragit® S 100 dispersion applied to the antibiotic matrix pellets is provided below in Table 3.

TABLE 3

Eudragit ® S 100 Aqueous Coating Dispersion

| Component | Percentage (%) |
|---|---|
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

B. Preparation Procedure for an Eudragit® S 100 Aqueous Dispersion Part 1:

(i) Dispense Eudragit® S 100 powder in deionized water with stirring.

(ii) Add ammonium hydroxide solution drop-wise into the dispersion with stirring.

(iii) Allow the partially neutralized dispersion to stir for 60 minutes.

(iv) Add triethyl citrate drop-wise into the dispersion with stirring. Stir for about 2 hours prior to the addition of Part B.

Part II:

(i) Disperse talc in the required amount of water (ii) Homogenize the dispersion using a PowerGen 700D high shear mixer.

(iii) Part B is then added slowly to the polymer dispersion in Part A with a mild stirring.

1.5 Coating Conditions for the Application of Aqueous Coating Dispersions

The following coating parameters are used to coat matrix pellets with each of the Eudragit® L 30 D-55 and Eudragit® S 100 aqueous film coating.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.

(ii) Coat matrix pellets with S100 dispersion such that you apply 20% coat weight gain to the pellets.

1.6 Encapsulation of the Antibiotic Pellets

Pellets are filled into size 00 hard gelatin capsules at a ratio of 30%: 30%: 40%: Immediate-release matrix pellets uncoated, L30 D-55 coated pellets and S100 coated pellets respectively. The capsule is filled with the three different pellets to achieve a the desire dosage.

The immediate release matrix pellets include the first antibiotic, the L30 D-55 coated pellets are made by coating matrix pellets that contain the second antibiotic and the S100 coated pellets are made by coating matrix pellets that contain the first antibiotic.

Three Pulses

Example 44

Antibiotic Pellet Formulation and Preparation Procedure 44.1 Pellet Formulations for subsequent coating The composition of the Antibiotictrihydrate matrix pellets provided in Table 4.

TABLE 4

Composition of AntibioticMatrix Pellets

| Component | Percentage (%) |
|---|---|
| Antibiotic Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

44.2 Preparation Procedure for AntibioticMatrix Pellets 44.2.1 Blend Antibioticand Avicel® PH 101 using a low shear blender.

44.2.2 Add the hydroxypropyl methylcellulose binder solution slowly into the powder blend under continuous mixing.

44.2.3 Extrude the wet mass using an LCI Bench Top Granulator. The diameter of the screen of the Bench Top Granulator is 0.8 mm.

44.2.4 Spheronize the extrudate using a QJ-230 Spheronizer using a small cross section plate.

44.2.5 Dry the spheronized pellets at 60° C. using a fluid bed dryer until the exhaust temperature reaches 40° C.

44.2.6 Pellets between 20 and 40 Mesh were collected for fturther processing.

44.2.7 The above procedure is used to produce pellets that contain a first antibiotic and pellets that contain a second and different antibiotic.

44.3 Preparation of an Eudragit® L 30 D-55 Aqueous Coating Dispersion 44.3.1 Dispersion Formulation The composition of the aqueous Eudragit L30D-55 dispersion applied to the Antibioticmatrix pellets is provided below in Table 5.

TABLE 5

Eudragit ® L 30 D-55 Aqueous Coating Dispersion

| Component | Percentage (%) |
|---|---|
| Eudragit ® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

44.4 Preparation Procedure for an Eudragit® L 30 D-55 Aqueous Dispersion 44.4.1 Suspend triethyl citrate and talc in deionized water.

44.4.2 The TEC/talc suspension is mixed using laboratory mixer.

44.4.3 Add the TEC/talc suspension from slowly to the Eudragit® L 30 D-55 latex dispersion while stirring.

44.4.4 Allow the coating dispersion to stir for one hour prior to application onto the Antibioticmatrix pellets.

44.5 Preparation of an Eudragit® S 100 Aqueous Coating Dispersion 44.5.1 Dispersion Formulation The composition of the aqueous Eudragit® S 100 dispersion applied to the Antibioticmatrix pellets is provided below in Table 6.

TABLE 6

Eudragit ® S 100 Aqueous Coating Dispersion

| Component | Percentage (%) |
|---|---|
| Part A | |
| Eudragit ® 100 | 10.0 |
| 1 N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

44.6 Preparation Procedure for an Eudragit® S 100 Aqueous Dispersion

Part A:

44.6.1 Dispense Eudragit® S 100 powder in deionized water with stirring.

44.6.2 Add ammonium hydroxide solution drop-wise into the dispersion with stirring.

44.6.3 Allow the partially neutralized dispersion to stir for 60 minutes.

44.6.4 Add triethyl citrate drop-wise into the dispersion with stirring and let stir overnight prior to the addition of Part B.

Part B:

44.6.5 Disperse talc in the required amount of water 44.6.6 Stir the dispersion using an overhead laboratory mixer.

44.6.7 Part B is then added slowly to the polymer dispersion in Part A with a mild stirring.

44.7 Coating Conditions for the Application of Aqueous Coating Dispersions

The following coating parameters are used for both the Eudragite® L 30 D-55 and Eudragit® S 100 aqueous film coating processes.

Coating Equipment STREA 1™ Table Top Laboratory Fluid Bed Coater

Spray nozzle diameter 1.0 mm

Material Charge 300 gram

Inlet Air Temperature 40 to 45° C.

Outlet Air Temperature 30 to 33° C.

Atomization Air Pressure 1.8 Bar

Pump Rate 2–6 gram per minute 44.7.1 Coat matrix pellets with L30 D-55 dispersion such that you apply 20% coat weight gain to the pellets.

44.7.2 Coat matrix pellets with S100 dispersion such that you apply 37% coat weight gain to the pellets.

44.8 Preparation of AntibioticGranulation (Immediate Release Component) for tabletting

TABLE 7

Composition of Antibiotic Granulation

| Component | Percentage (%) |
|---|---|
| Antibiotic Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

44.8.1 Blend Antibioticand Avicel® PH 101 using a low shear blender.

44.8.2 Add the hydroxypropyl methylcellulose binder solution slowly into the powder blend under continuous mixing.

44.8.3 Dry the granulation at 60° C. using a fluid bed dryer until the exhaust temperature reaches 40° C.

44.8.4 Granules between 20 and 40 Mesh are collected for further processing.

44.9 Tabletting of the AntibioticPellets

TABLE 8

Composition of Antibiotic Tablets

| Component | Percentage (%) |
|---|---|
| First antibiotic granules | 32.5 |
| Avicel PH 200 | 5.0 |
| Second antibiotic L30D-55 coated pellets | 30 |
| First antibiotic S100 coated pellets | 30 |
| Colloidal silicon dioxide | 1.5 |
| Magnesium stearate | 1.0 |
| Total | 100 |

44.9.1 Blend the Antibioticgranules, Avicel PH-200, Antibioticpellets and colloidal silicon dioxide for 15 minutes in a tumble blender.

44.9.2 Add the magnesium stearate to the blender, and blend for 5 minutes.

44.9.3 Compress the blend on a rotary tablet press.

44.9.4 The fill weight should be adjusted to achieve the desired dosage.

Four pulses

Example 45

1 Antibiotic Matrix Pellet Formulation and Preparation Procedure

45.1 Pellet Formulation

The composition of the antibiotic matrix pellets provided in Table 9.

TABLE 9

| Composition of Antibiotic Pellets | |
|---|---|
| Component | Percentage (%) |
| Antibiotic | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

45.2 Preparation Procedure for Antibiotic Matrix Pellets 45.2.1 Blend antibiotic and Avicel® PH 1O 1 using a Robot Coupe high shear granulator.

45.2.2 Add 20% Povidone K29/32 binder solution slowly into the powder blend under continuous mixing.

45.2.3 Extrude the wet mass using an LCI Bench Top Granulator. The diameter of the screen of the Bench Top Granulator was 1.0 mm.

45.2.4 Spheronize the extrudate using a Model SPH20 Caleva Spheronizer.

45.2.5 Dry the spheronized pellets at 50° C. overnight.

45.2.6 Pellets between 16 and 30 Mesh were collected for further processing.

45.2.7 The above procedure is used to prepare pellets that contain a first antibiotic and pellets that contain a second antibiotic.

45.3 Preparation of an Eudragit® L 30 D-55 Aqueous Coating Dispersion 45.3.1 Dispersion Formulation The composition of the aqueous Eudragit L30D-55 dispersion applied to the antibiotic matrix pellets is provided below in Table 10.

TABLE 10

| Eudragit ® L 30 D-55 Aqueous Coating Dispersion | |
|---|---|
| Component | Percentage (%) |
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

45.4 Preparation Procedure for an Eudragit® L 30 D-55 Aqueous Dispersion 45.4.1 Suspend triethyl citrate and talc in deionized water.

45.4.2 The TEC/talc suspension is then homogenized using a PowerGen 700 high shear mixer.

45.4.3 Add the TEC/talc suspension slowly to the Eudragit® L 30 D-55 latex dispersion while stirring.

45.4.4 Allow the coating dispersion to stir for one hour prior to application onto the antibiotic matrix pellets.

45.5 Preparation of an Eudragit® S 100 Aqueous Coating Dispersion 45.5.1 Dispersion Formulation The composition of the aqueous Eudragit® S 100 dispersion applied to the antibiotic matrix pellets is provided below in Table 11.

TABLE 11

| Eudragit ® S 100 Aqueous Coating Dispersion | |
|---|---|
| Component | Percentage (%) |
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

45.6 Preparation Procedure for an Eudragit® S 100 Aqueous Dispersion

Part A:

45.6.1 Dispense Eudragit® S 100 powder in deionized water with stirring.

45.6.2 Add ammonium hydroxide solution drop-wise into the dispersion with stirring.

45.6.3 Allow the partially neutralized dispersion to stir for 60 minutes.

45.6.4 Add triethyl citrate drop-wise into the dispersion with stirring. Stir for about 2 hours prior to the addition of Part B.

Part B:

45.6.5 Disperse talc in the required amount of water 45.6.6 Homogenize the dispersion using a PowerGen 700D high shear mixer.

45.6.7 Part B is then added slowly to the polymer dispersion in Part A with a mild stirring.

45.7 Coating Conditions for the Application of Aqueous Coating Dispersions

The following coating parameters are used for coating with each of the Eudragit® L 30 D-55 and Eudragit® S 100 aqueous film coatings.

| | |
|---|---|
| Coating Equipment | STREA 1 ™ Table Top Laboratory Fluid Bed Coater |
| Spray nozzle diameter | 1.0 mm |

-continued

| | |
|---|---|
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

45.7.1 Coat matrix pellets with L30 D-55 dispersion such that you apply 12% coat weight gain to the pellets.

45.7.2 Coat matrix pellets with L30 D-55 dispersion such that you apply 30% coat weight gain to the pellets.

45.7.3 Coat matrix pellets with S100 dispersion such that you apply 20% coat weight gain to the pellets.

45.8 Encapsulation of the Antibiotic Pellets

Pellets are filled into size 00 hard gelatin capsules at a ratio of 20%: 30%: 20%: 30% Immediate-release matrix pellets (uncoated), L30 D-55 coated pellets 12% weight gain, L30D-55 coated pellets 30% weight gain and S 100 coated pellets respectively. The capsule is filled with the four different pellets to achieve the desired dosage.

The immediate release pellets contain the first antibiotic; the L30 D-55 12% weight gain coated pellets containe the second antibiotic; the L30 D-55 30% weight gain coated pellets contain the first antibiotic and the S100 coated pellets contain the second antibiotic.

Example 46

Amoxicillin Pellet Formulation and Preparation Procedure

Pellet Formulations

The composition of the Amoxicillin trihydrate pellets provided in Table 12.

TABLE 12

Composition of Amoxicillin Pellets

| Component | Percentage (%) |
|---|---|
| Amoxicillin Trihydrate powder | 92 |
| Avicel PH 101 | 6.0 |
| Polyoxyl 35 Castor Oil* | 1.0 |
| Hydroxypropyl methylcellulose, NF* | 1.0 |
| Purified Water | ** |
| Total | 100 |

*Hydroxypropyl methylcellulose and Cremaphor EL were added as a 2.9% w/w aqueous solution during wet massing.
**Removed during processing Preparation Procedure for Amoxicillin Pellets Blend Amoxicillin and Avicel® PH 101 using a low shear blender.

Add the hydroxypropyl methylcellulose and Polyoxyl 35 Castor Oil binder solution slowly into the powder blend under continuous mixing.

Extrude the wet mass using an LCI Bench Top Granulator. The diameter of the screen of the Bench Top Granulator is 0.8 mm.

Spheronize the extrudate using a QJ-230 Spheronizer using a small cross section plate.

Dry the spheronized pellets at 600° C. using a fluid bed dryer until the exhaust temperature reaches 40° C.

Pellets between 20 and 40 Mesh were collected for further processing.

Amoxicillin Enteric-Release Pellet Formulation and Preparation Procedure

Preparation of an Eudragit® L 30 D-55/Eudragit NE 30D Aqueous Coating Dispersion Dispersion Formulation The composition of the aqueous Eudragit L30D-55/Eudragit NE 30D aqueous coating dispersion applied to the amoxicillin pellets is provided below in Table 13.

TABLE 13

Eudragit ® L 30 D-S55/Eudragit NE 30D Aqueous Coating Dispersion

| Component | Percentage (%) |
|---|---|
| Eudragit ® L 30D-55 | 44.4 |
| Eudragit NE 30D | 14.8 |
| Triethyl Citrate | 1.3 |
| Imwitor 900 | 0.9 |
| Purified Water* | 38.6 |
| Solid Content | 20.6 |
| Polymer Content | 16.4 |

*Removed during processing

Preparation Procedure for an Eudragit® L 30D-55/Eudragit NE 30D Aqueous Dispersion Heat purified water to 75–80° C. and then add triethyl citrate (TEC) and Imwitor 900. Homogenize dispersion until temperature is less than 55° C.

The TEC/Imwitor 900 dispersion is then stirred until the temperature is less than 35° C.

Add the TEC/Imwitor 900 dispersion to Eudragit L30D-55 latex dispersion and stir for at least 30 minutes.

Add Eudragit NE 30D to the Eudragit L30D/TEC/Imwitor 900 dispersion and stir for at least 10 minutes.

Screen the dispersion through a No. 60 mesh sieve prior to coating.

Continue to stir the dispersion until the coating process is complete.

Coating Conditions for the Application of Eudragit L30D-55/Eudragit NE 30D Aqueous Coating Dispersion The following coating parameters were used for coating of the Eudragit® L 30 D-55/ Eudragit NE30D film coating dispersion.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 45° C. |
| Outlet Air Temperature | 32 to 35° C. |
| Atomization Air Pressure | 1.6 Bar |
| Pump Rate | 3–4 gram per minute |

Coat Amoxicillin pellets with Eudragit L30 D-55/Eudragit NE 30D film coating dispersion such that you apply 20% coat weight gain to the pellets.

Amoxicillin Delayed Enteric-Release Pellets Formulation and Preparation Procedure Preparation of an AQOAT AS-HF Aqueous Coating Dispersion Dispersion Formulation The composition of the aqueous AQOAT AS-HF aqueous coating dispersion applied to the amoxicillin pellets is provided below in Table 14.

TABLE 14

AQOAT AS-HF Aqueous Coating Dispersion

| Component | Percentage (%) |
|---|---|
| AQOAT AS-HF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-HF Aqueous Dispersion

Add triethyl citrate (TEC) to the purified water with stirring.

Add the sodium lauryl sulfate (SLS) to the TEC dispersion with stirring and completely until completely dissolved.

Add the AQOAT to the TEC/SLS dispersion and stir for at least 30 minutes.

Add the talc to the AQOAT dispersion and until completely mixed and for at least 30 minutes.

Screen the dispersion through a No. 60 mesh sieve prior to coating.

Continue to stir the dispersion until the coating process is complete.

Coating Conditions for the Application of AQOAT AS-HF Aqueous Coating Dispersion The following coating parameters were used for coating of the AQOAT AS-HF film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat amoxicillin pellets with AQOAT AS-HF film coating dispersion such that you apply 30–35% coat weight gain to the pellets.

Amoxicillin Colonic-Release Pellet Formulation and Preparation Procedure

Preparation of an Eudragit® FS 30D Aqueous Coating Dispersion

Dispersion Formulation

The composition of the aqueous Eudragit® FS 30D dispersion applied to the Amoxicillin pellets is provided below in Table 15.

TABLE 15

Eudragit ® FS 30D Aqueous Coating Dispersion

| Component | Percentage (%) |
|---|---|
| Eudragit ® FS 30D | 54.8 |
| Triethyl Citrate | 0.9 |
| Talc | 3.3 |
| Purified Water* | 41.0 |

TABLE 15-continued

Eudragit ® FS 30D Aqueous Coating Dispersion

| Component | Percentage (%) |
|---|---|
| Solid Content | 20.6 |
| Polymer Content | 16.4 |

*Removed during processing

Preparation Procedure for an Eudragit® FS 30D Aqueous Dispersion

Disperse triethyl citrate (TEC) in the purified water.

Add the talc in the triethyl citrate dispersion.

Homogenize the dispersion using a homogenizer.

Add slowly the Eudragit® FS 30D dispersion to the talc/TEC dispersion with stirring.

Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| Coating Equipment | STREA 1 ™ Table Top Laboratory Fluid Bed Coater |
|---|---|
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Clarithromycin Pellet Formulation and Preparation Procedure

Pellet Formulation

The composition of the clarithromycin pellets provided in Table 16.

TABLE 16

Composition of Clarithromycin Pellets

| Component | Percentage (%) |
|---|---|
| Clarithromycin | 77.0 |
| Lactose monohydrate, spray dried | 11.0 |
| Croscarmellose sodium | 5.0 |
| Polyoxyl 35 Castor Oil* | 5.0 |
| Hydroxypropyl methylcellulose* | 2.0 |
| Purified water | * |
| Total | 100 |

*Removed during processing

Preparation Procedure for Clarithromycin Pellets

Prepare the binder solution by adding the Polyoxyl to the purified water while stirring. After that is mixed, slowly add the hydroxypropyl methylcellulose and continue to stir until a solution is achieved.

Blend clarithromycin, lactose monohydrate, and croscarmellose sodium using a Robot Coupe high shear granulator.

Add binder solution slowly into the powder blend under continuous mixing.

Granulate the powders in the high shear granulator with the binder solution.

Extrude the wet mass using an LCI Bench Top Granulator. The diameter of the screen of the Bench Top Granulator was 1.0 mm.

Spheronize the extrudate using a Model SPH20 Caleva Spheronizer.

Dry the spheronized pellets at 50° C. until the moisture level is >3%.

Pellets between 16 and 30 Mesh were collected for further processing.

Clarithromycin Enteric-Release Pellet Formulation and Preparation Procedure

Preparation of an Eudragit® L 30 D-55/Eudragit NE 30D Aqueous Coating Dispersion Dispersion Formulation The composition of the aqueous Eudragit L30D-55/ Eudragit NE 30D aqueous coating dispersion applied to the clarithromycin pellets is provided below in Table 17.

TABLE 17

Eudragit ® L 30 D-55/Eudragit NE 30D Aqueous Coating Dispersion

| Component | Percentage (%) |
|---|---|
| Eudragit ® L 30D-55 | 44.4 |
| Eudragit NE 30D | 14.8 |
| Triethyl Citrate | 1.3 |
| Imwitor 900 | 0.9 |
| Purified Water* | 38.6 |
| Solid Content | 20.6 |
| Polymer Content | 16.4 |

*Removed during processing

Preparation Procedure for an Eudragit® L 30D-55/Eudragit NE 30D Aqueous Dispersion Heat purified water to 75–80° C. and then add triethyl citrate (TEC) and Imwitor 900. Homogenize dispersion until temperature is less than 55° C.

The TEC/Imwitor 900 dispersion is then stirred until the temperature is less than 35° C.

Add the TEC/Imwitor 900 dispersion to Eudragit L30D-55 latex dispersion and stir for at least 30 minutes.

Add Eudragit NE 30D to the Eudragit L30D/TEC/Imwitor 900 dispersion and stir for at least 10 minutes.

Screen the dispersion through a No. 60 mesh sieve prior to coating.

Continue to stir the dispersion until the coating process is complete.

Coating Conditions for the Application of Eudragit L30D-55/Eudragit NE 30D Aqueous Coating Dispersion The following coating parameters were used for coating of the Eudragit® L 30 D-55/Eudragit NE30D film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 45° C. |
| Outlet Air Temperature | 32 to 35° C. |
| Atomization Air Pressure | 1.6 Bar |
| Pump Rate | 3–4 gram per minute |

Coat clarithromycin pellets with Eudragit L30 D-55/ Eudragit NE 30D film coating dispersion such that you apply 20% coat weight gain to the pellets.

Clarithromycin Delayed Enteric-Release Pellets Formulation and Preparation Procedure Preparation of an AQOAT AS-HF Aqueous Coating Dispersion Dispersion Formulation The composition of the aqueous AQOAT AS-HF aqueous coating dispersion applied to the clarithromycin pellets is provided below in Table 18.

TABLE 18

AQOAT AS-HF Aqueous Coating Dispersion

| Component | Percentage (%) |
|---|---|
| AQOAT AS-HF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-HF Aqueous Dispersion

Add triethyl citrate (TEC) to the purified water with stirring.

Add the sodium lauryl sulfate (SLS) to the TEC dispersion with stirring and completely until completely dissolved.

Add the AQOAT to the TEC/SLS dispersion and stir for at least 30 minutes.

Add the talc to the AQOAT dispersion and until completely mixed and for at least 30 minutes.

Screen the dispersion through a No. 60 mesh sieve prior to coating.

Continue to stir the dispersion until the coating process is complete.

Coating Conditions for the Application of AQOAT AS-HF Aqueous Coating Dispersion The following coating parameters were used for coating of the AQOAT AS-HF film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat clarithromycin pellets with AQOAT AS-HF film coating dispersion such that you apply 30–35% coat weight gain to the pellets.

Clarithromycin Colonic-Release Pellets Formulation and Preparation Procedure

Preparation of an Eudragit® FS30D Aqueous Coating Dispersion

Dispersion Formulation

The composition of the aqueous Eudragit® FS 30D dispersion applied to the clarithromycin pellets is provided below in Table 19.

TABLE 19

Eudragit® FS 30D Aqueous Coating Dispersion

| Component | Percentage (%) |
|---|---|
| Eudragit® FS 300 | 54.8 |
| Triethyl Citrate | 0.9 |
| Talc | 3.3 |
| Purified Water* | 41.0 |
| Solid Content | 20.6 |
| Polymer Content | 16.4 |

*Removed during processing

Preparation Procedure for an Eudragit® FS 30D Aqueous Dispersion

Disperse triethyl citrate (TEC) in the purified water.
Add the talc in the triethyl citrate dispersion.
Homogenize the dispersion using a homogenizer.
Add slowly the Eudragit® FS 30D dispersion to the talc/TEC dispersion with stirring.
Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| Coating Equipment | STREA 1 ™ Table Top Laboratory Fluid Bed Coater |
|---|---|
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Amoxicillin and Clarithromycin Tablets
Preparation of Amoxicillin and Clarithromycin Granulation for tableting

TABLE 20

Composition of Amoxicillin and Clarithromycin Granulation (Immediate Release)

| Component | Percentage (%) |
|---|---|
| Amoxicillin Trihydrate powder | 22.0 |
| Clarithromycin | 22.0 |
| Lactose monohydrate, spray dried | 45.0 |
| Avicel PH 101 | 10.0 |
| Hydroxypropyl methylcellulose, NF* | 1.0 |
| Total | 100 |

*Hydroxypropyl methylcellulose was added as a 2.9% w/w aqueous solution during wet massing.

Blend Amoxicillin, Clarithromycin, lactose, and Avicel® PH 101 using a high shear mixer.
Add the hydroxypropyl methylcellulose binder solution slowly into the powder blend under continuous mixing.
Dry the granulation at 60° C. using a fluid bed dryer until the exhaust temperature reaches 40° C.
Granules between 20 and 40 Mesh are collected for further processing.

Tableting of the Amoxicillin and Clarithromycin

TABLE 21

Composition of Amoxicillin and Clarithromycin Tablets

| Component | Percentage (%) |
|---|---|
| Amoxicillin/Clarithromycin granules | 45.0 |
| Avicel PH 200 | 7.5 |
| Eudragit L30D-55/NE 30D coated Amoxicillin Pellets | 6.4 |
| Eudragit L30D-55/NE 30D coated Clarithromycin Pellets | 7.6 |
| AQOAT coated Amoxicillin Pellets | 7.2 |
| AQOAT coated Clarithromycin Pellets | 8.6 |
| Eudragit FS 30D coated Amoxicillin Pellets | 6.9 |
| Eudragit FS 30D coated Clarithromycin Pellets | 8.3 |
| Colloidal silicon dioxide | 1.5 |
| Magnesium stearate | 1.0 |
| Total | 100 |

Blend the Amoxicillin/Clarithromycin granules, Avicel PH-200, Amoxicillin coated pellets, Clarithromycin coated pellets and colloidal silicon dioxide for 15 minutes in a tumble blender.
Add the magnesium stearate to the blender, and blend for 5 minutes.
Compress the blend on a rotary tablet press.
The fill weight should be adjusted to achieve a 500 mg total dose tablet.

Example 47

Amoxicillin Pellet Formulation and Preparation Procedure

Pellet Formulations
The composition of the Amoxicillin trihydrate pellets provided in Table 22.

TABLE 22

Composition of Amoxicillin Pellets

| Component | Percentage (%) |
|---|---|
| Amoxicillin Trihydrate powder | 92 |
| Avicel PH 101 | 6.0 |
| Polyoxyl 35 Castor Oil* | 1.0 |
| Hydroxypropyl methylcellulose, NF* | 1.0 |
| Purified Water | ** |
| Total | 100 |

*Hydroxypropyl methylcellulose and Cremaphor EL were added as a 2.9% w/w aqueous solution during wet massing.
**Removed during processing Preparation Procedure for Amoxicillin Pellets
Blend Amoxicillin and Avicel® PH 101 using a low shear blender.
Add the hydroxypropyl methylcellulose and Polyoxyl 35 Castor Oil binder solution slowly into the powder blend under continuous mixing.
Extrude the wet mass using an LCI Bench Top Granulator. The diameter of the screen of the Bench Top Granulator is 0.8 mm.
Spheronize the extrudate using a QJ-230 Spheronizer using a small cross section plate.
Dry the spheronized pellets at 60° C. using a fluid bed dryer until the exhaust temperature reaches 40° C.
Pellets between 20 and 40 Mesh were collected for further processing.

Amoxicillin Delayed Enteric-Release Pellets
Formulation and Preparation Procedure Preparation of an AQOAT AS-HF Aqueous Coating Dispersion Dispersion Formulation The composition of the aqueous AQOAT AS-HF aqueous coating dispersion applied to the amoxicillin pellets is provided below in Table 23.

TABLE 23

AQOAT AS-HF Aqueous Coating Dispersion

| Component | Percentage (%) |
|---|---|
| AQOAT AS-HF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-HF Aqueous Dispersion

Add triethyl citrate (TEC) to the purified water with stirring.

Add the sodium lauryl sulfate (SLS) to the TEC dispersion with stirring and completely until completely dissolved.

Add the AQOAT to the TEC/SLS dispersion and stir for at least 30 minutes.

dd the talc to the AQOAT dispersion and until completely mixed and for at least 30 minutes.

Screen the dispersion through a No. 60 mesh sieve prior to coating.

Continue to stir the dispersion until the coating process is complete.

Coating Conditions for the Application of AQOAT AS-HF Aqueous Coating Dispersion The following coating parameters were used for coating of the AQOAT AS-HF film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat amoxicillin pellets with AQOAT AS-HF film coating dispersion such that you apply 30–35% coat weight gain to the pellets.

Clarithromycin Pellet Formulation and Preparation Procedure

Pellet Formulation

The composition of the clarithromycin pellets provided in Table 24.

TABLE 24

Composition of Clarithromycin Pellets

| Component | Percentage (%) |
|---|---|
| Clarithromycin | 77.0 |
| Lactose monohydrate, spray dried | 11.0 |

TABLE 24-continued

Composition of Clarithromycin Pellets

| Component | Percentage (%) |
|---|---|
| Croscarmellose sodium | 5.0 |
| Polyoxyl 35 Castor Oil* | 5.0 |
| Hydroxypropyl methylcellulose* | 2.0 |
| Purified water | * |
| Total | 100 |

*Removed during processing

Preparation Procedure for Clarithromycin Pellets

Prepare the binder solution by adding the Polyoxyl to the purified water while stirring. After that is mixed, slowly add the hydroxypropyl methylcellulose and continue to stir until a solution is achieved.

Blend clarithromycin, lactose monohydrate, and croscarmellose sodium using a Robot Coupe high shear granulator.

Add binder solution slowly into the powder blend under continuous mixing.

Granulate the powders in the high shear granulator with the binder solution.

Extrude the wet mass using an LCI Bench Top Granulator. The diameter of the screen of the Bench Top Granulator was 1.0 mm.

Spheronize the extrudate using a Model SPH20 Caleva Spheronizer.

Dry the spheronized pellets at 50° C. until the moisture level is >3%.

Pellets between 16 and 30 Mesh were collected for further processing.

Clarithromycin Enteric-Release Pellet Formulation
and Preparation Procedure

Preparation of an Eudragit® L 30 D-55/Eudragit NE 30D Aqueous Coating Dispersion Dispersion Formulation The composition of the aqueous Eudragit L30D-55/Eudragit NE 30D aqueous coating dispersion applied to the clarithromycin pellets is provided below in Table 25.

TABLE 25

Eudragit ® L 30D-55/Eudragit NE 30D Aqueous Coating Dispersion

| Component | Percentage (%) |
|---|---|
| Eudragit ® L 30D-55 | 44.4 |
| Eudragit NE 30D | 14.8 |
| Triethyl Citrate | 1.3 |
| Imwitor 900 | 0.9 |
| Purified Water* | 38.6 |
| Solid Content | 20.6 |
| Polymer Content | 16.4 |

*Removed during processing

Preparation Procedure for an Eudragit® L 30D-55/Eudragit NE 30D Aqueous Dispersion Heat purified water to 75–80° C. and then add triethyl citrate (TEC) and Imwitor 900. Homogenize dispersion until temperature is less than 55° C.

The TEC/Imwitor 900 dispersion is then stirred until the temperature is less than 35° C.

Add the TEC/Imwitor 900 dispersion to Eudragit L30D-55 latex dispersion and stir for at least 30 minutes.

Add Eudragit NE 30D to the Eudragit L30D/TEC/ Imwitor 900 dispersion and stir for at least 10 minutes.

Screen the dispersion through a No. 60 mesh sieve prior to coating.

Continue to stir the dispersion until the coating process is complete.

Coating Conditions for the Application of Eudragit L30D-55/Eudragit NE 30D Aqueous Coating Dispersion The following coating parameters were used for coating of the Eudragit® L 30 D-55/Eudragit NE30D film coating dispersion.

| Coating Equipment | STREA 1 ™ Table Top Laboratory Fluid Bed Coater |
| --- | --- |
| Spray nozzle diameter | 1.0 mm |
| Material Charge | 300 gram |
| Inlet Air Temperature | 45° C. |
| Outlet Air Temperature | 32 to 35° C. |
| Atomization Air Pressure | 1.6 Bar |
| Pump Rate | 3–4 gram per minute |

Coat clarithromycin pellets with Eudragit L30 D-55/ Eudragit NE 30D film coating dispersion such that you apply 20% coat weight gain to the pellets.

Clarithromycin Colonic-Release Pellets Formulation and Preparation Procedure

Preparation of an Eudragit® FS30D Aqueous Coating Dispersion

Dispersion Formulation

The composition of the aqueous Eudragit® FS 30D dispersion applied to the clarithromycin pellets is provided below in Table 26.

TABLE 26

| Eudragit ® FS 30D Aqueous Coating Dispersion | |
| --- | --- |
| Component | Percentage (%) |
| Eudragit ® FS 30D | 54.8 |
| Triethyl Citrate | 0.9 |
| Talc | 3.3 |
| Purified Water* | 41.0 |
| Solid Content | 20.6 |
| Polymer Content | 16.4 |

*Removed during processing

Preparation Procedure for an Eudragit® FS 30D Aqueous Dispersion

Disperse triethyl citrate (TEC) in the purified water.

Add the talc in the triethyl citrate dispersion.

Homogenize the dispersion using a homogenizer.

Add slowly the Eudragit® FS 30D dispersion to the talc/TEC dispersion with stirring.

Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| Coating Equipment | STREA 1 ™ Table Top Laboratory Fluid Bed Coater |
| --- | --- |
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Amoxicillin and Clarithromycin Tablets
Preparation of Amoxicillin Granulation for tableting

TABLE 27

| Composition of Amoxicillin Granulation (Immediate Release) | |
| --- | --- |
| Component | Percentage (%) |
| Amoxicillin Trihydrate powder | 22.0 |
| Lactose monohydrate, spray dried | 57.0 |
| Avicel PH 101 | 20.0 |
| Hydroxypropyl methylcellulose, NF* | 1.0 |
| Total | 100 |

*Hydroxypropyl methylcellulose was added as a 2.9% w/w aqueous solution during wet massing.

Blend Amoxicillin, lactose, and Avicel® PH 101 using a high shear mixer.

Add the hydroxypropyl methylcellulose binder solution slowly into the powder blend under continuous mixing.

Dry the granulation at 60° C. using a fluid bed dryer until the exhaust temperature reaches 40° C.

Granules between 20 and 40 Mesh are collected for further processing.

Tableting of the Amoxicillin and Clarithromycin

TABLE 28

| Composition of Amoxicillin and Clarithromycin Tablets | |
| --- | --- |
| Component | Percentage (%) |
| Amoxicillin granules | 45.0 |
| Avicel PH 200 | 7.5 |
| Eudragit L30D-55/NE 30D coated Clarithromycin Pellets | 14.9 |
| AQOAT coated Amoxicillin Pellets | 14.0 |
| Eudragit FS 30D coated Clarithromycin Pellets | 16.1 |
| Colloidal silicon dioxide | 1.5 |
| Magnesium stearate | 1.0 |
| Total | 100 |

Blend the Amoxicillin granules, Avicel PH-200, Amoxicillin coated pellets, Clarithromycin coated pellets and colloidal silicon dioxide for 15 minutes in a tumble blender.

Add the magnesium stearate to the blender, and blend for 5 minutes.

Compress the blend on a rotary tablet press.

The fill weight should be adjusted to achieve a 500 mg total dose tablet.

In one embodiment, Amoxicillin will be dosed in an alternate pulse to Clarithromycin. This will alternate the exposure to the bacteria in such a way as to make both antibiotics more effective than if they were co-administered, and thereby competing with each other for sites on the bacterial cell wall receptors, or sites within the bacterial cells.

In addition, even when Amoxicillin and Clarithromycin are not delivered in alternate pulses, the dosage forms as hereinabove described provide for improved treatment of infection.

Numerous modifications and variations of the present invention are possible in light of the above teachings; therefore, within the scope of the appended claims, the invention may be practiced otherwise than as particularly described.

What is claimed is:

1. A once-a-day antibiotic product comprising: first, second, and third dosage forms, wherein each of said dosage forms includes at least one antibiotic and a pharmaceutically acceptable carrier; one of said dosage forms includes at least a first antibiotic and another of said dosage forms includes at least a second antibiotic that is different from the first antibiotic; wherein said first and second antibiotics are each selected from the group consisting of Amoxicillin and Clarithromycin; and wherein when said first antibiotic is Amoxicillin said second antibiotic is Clarithromycin; and wherein when said first antibiotic is Clarithromycin said second antibiotic is Amoxicillin; said first dosage form is an immediate release dosage form; said second and third dosage forms are delayed release dosage forms; each of said first, second, and third dosage forms initiates release of antibiotic at different times and Cmax in serum of the total antibiotic released from said antibiotic product is achieved in less than about 12 hours from administration; and said once-a-day antibiotic product contains the total dosage of said first and second antibiotics for a twenty-four hour period.

2. The product of claim 1, wherein antibiotic released from the second dosage form reaches a Cmax in serum after antibiotic released from the first dosage reaches a Cmax in serum.

3. The product of claim 2, wherein antibiotic released form the third dosage form reaches a Cmax in serum after antibiotic released from the second dosage form reaches Cmax in serum.

4. The product of claim 1, wherein the first dosage form includes the first antibiotic, the second dosage form includes the first and second antibiotics, and the third dosage form includes the second antibiotic.

5. The product of claim 1, wherein the immediate release dosage form contains from 20% to 50% of the total dosage of antibiotic.

6. The product of claim 1, wherein said second dosage form initiates release of antibiotic before said third dosage form, wherein said second dosage form provides from 30% to 60% by weight of the total antibiotic released by said second and third dosage forms, and wherein said third dosage form provides the remainder of the total antibiotic released by said second and third dosage forms.

7. The product of claim 1, wherein antibiotic released from the second dosage form reaches a Cmax in serum in no more than about 4 hours after administration of the product.

8. The product of claim 1, wherein antibiotic released from the third dosage form reaches a Cmax in serum within 8 hours after administration of the product.

9. The product of claim 1, wherein the product is an oral dosage form.

10. The product of claim 1, further comprising a fourth dosage form, said fourth dosage form comprising at least one of said first and second antibiotics and a pharmaceutically acceptable carrier.

11. The product of claim 1, further comprising: a fourth dosage form, and wherein said first dosage form contains said first antibiotic; said second dosage form contains said first antibiotic; said third dosage form contains said second antibiotic; said fourth dosage form includes said second antibiotic and a pharmaceutically acceptable carrier; and said second and third dosage forms have release profiles whereby $C_{max}$ in serum for the first antibiotic and $C_{max}$ in serum for the second antibiotic released from the second and third dosage forms respectively are reached later in time than $C_{max}$ in serum is reached for the first antibiotic released from the first dosage form, and whereby the $C_{max}$ in serum for the second antibiotic released from the fourth dosage form is reached at a time after $C_{max}$ in serum for antibiotic released from each of the first, second, and third dosage forms are reached.

12. The product of claim 11, wherein the first antibiotic released from the second dosage form, and the second antibiotic released from the third dosage form reach a Cmax in serum at about the same time.

13. The product of claim 11, wherein said fourth dosage form is a sustained release dosage form.

14. The product of claim 11, wherein said fourth dosage form is a delayed release dosage form.

15. The product of claim 14, wherein the immediate release dosage form contains from 15% to 30% of the total dosage of antibiotic.

16. The product of claim 14, wherein said second dosage form initiates release of antibiotic before said third dosage form; wherein said third dosage form initiates release of antibiotic before said fourth dosage form; wherein said second dosage form provides 20% to 35% by weight of the total antibiotic released by said second, third, and fourth dosage forms; wherein said third dosage form provides from 20% to 40% by weight of the total antibiotic released by said second, third, and fourth dosage forms; and wherein said fourth dosage form provides the remainder of the total antibiotic released by said second, third, and fourth dosage forms.

17. The product of claim 11, wherein antibiotic released from the second dosage form reaches a Cmax in serum in no more than about 4 hours after administration of the product.

18. The product of claim 11, wherein antibiotic released from the third dosage form reaches a Cmax in serum within 8 hours after administration of the product.

19. The product of claim 11, wherein the product is an oral dosage form.

20. The antibiotic product of claim 1, wherein each of the first, second, and third dosage forms includes at least one of the first and second antibiotics.

21. The product of claim 20, wherein antibiotic released from the second dosage form reaches a Cmax in serum after antibiotic released from the first dosage form reaches a Cmax in serum.

22. The product of claim 20, wherein antibiotic released from the third dosage form reaches a Cmax in serum after antibiotic released from the second dosage form reaches a Cmax in serum.

23. The product of claim 20, wherein the immediate release dosage form contains from 20% to 50% of the total dosage of antibiotic.

24. The product of claim 20, wherein said second dosage form initiates release of antibiotic before said third dosage form, wherein said second dosage form provides from 30% to 60% by weight of the total antibiotic released by said second and third dosage forms, and wherein said third dosage form provides the remainder of the total antibiotic released by said second and third dosage forms.

25. The product of claim 20, wherein antibiotic released from the second dosage form reaches a Cmax in serum in no more than about 4 hours after administration of the product.

26. The product of claim 20, wherein antibiotic released from the third dosage form reaches a Cmax in serum within 8 hours after administration of the product.

27. The product of claim 20, wherein the product is an oral dosage form.

28. The product of claim 1, wherein each of the first, second, and third dosage forms contains a single antibiotic selected from the group consisting of Amoxicillin and Clarithtomycin.

29. The product of claim 2, wherein antibiotic released from the third dosage form reaches a Cmax in serum after antibiotic released from the second dosage form reaches a Cmax in serum.

30. The product of claim 28, wherein antibiotic released from the third dosage form reaches a Cmax in serum after antibiotic released from the second dosage form reaches a Cmax in serum, and wherein antibiotic released from the second dosage form reaches a Cmax in serum after antibiotic released from the first dosage form reaches a Cmax in serum.

31. The product of claim 28, wherein antibiotic released from the second dosage form reaches a Cmax in serum after antibiotic released from the first dosage form reaches a Cmax in serum.

32. A once-a-day antibiotic product comprising: first, second, third, and fourth dosage forms, wherein each of said dosage forms includes one of a first antibiotic and a second antibiotic, and a pharmaceutically acceptable carrier; wherein said first and second antibiotics are each selected from the group consisting of Amoxicillin and Clarithromycin; and wherein when said first antibiotic is Amoxicillin said second antibiotic is Clarithromycin; and wherein when said first antibiotic is Clarithromycin said second antibiotic is Amoxicillin; wherein the first dosage form contains said first antibiotic and is free of said second antibiotic; the second dosage form contains said second antibiotic and is free of said first antibiotic; the third dosage form contains said first antibiotic and is free of said second antibiotic; and said fourth dosage form contains said second antibiotic and is free of said first antibiotic; said first dosage form is an immediate release dosage form; said second, third, and fourth dosage forms are delayed release dosage forms; each of said first, second, third, and fourth dosage forms initiates release of antibiotic at different times and Cmax in serum of the total antibiotic released from said antibiotic product is achieved in less than about 12 hours from administration; and said once-a-day antibiotic product contains the total dosage of said first and second antibiotics for a twenty-four hour period.

33. The product of claim 32 wherein each of the first, second, third, and fourth dosage forms contains only one antibiotic.

34. A process for treating a bacterial infection in a host comprising:
administering to the host the antibiotic product of claim 1 once-a-day.

35. A process for treating a bacterial infection in a host comprising:
administering to the host the antibiotic product of claim 2 once-a-day.

36. A process for treating a bacterial infection in a host comprising:
administering to the host the antibiotic product of claim 3 once-a-day.

37. A process for treating a bacterial infection in a host comprising:
administering to the host the antibiotic product of claim 4 once-a-day.

38. A process for treating a bacterial infection in a host comprising:
administering to the host the antibiotic product of claim 5 once-a-day.

39. A process for treating a bacterial infection in a host comprising:
administering to the host the antibiotic product of claim 6 once-a-day.

40. A process for treating a bacterial infection in a host comprising:
administering to the host the antibiotic product of claim 7 once-a-day.

41. A process for treating a bacterial infection in a host comprising:
administering to the host the antibiotic product of claim 8 once-a-day.

42. A process for treating a bacterial infection in a host comprising:
administering to the host the antibiotic product of claim 9 once-a-day.

43. A process for treating a bacterial infection in a host comprising:
administering to the host the antibiotic product of claim 10 once-a-day.

44. A process for treating a bacterial infection in a host comprising:
administering to the host the antibiotic product of claim 11 once-a-day.

45. A process for treating a bacterial infection in a host comprising:
administering to the host the antibiotic product of claim 12 once-a-day.

46. A process for treating a bacterial infection in a host comprising:
administering to the host the antibiotic product of claim 13 once-a-day.

47. A process for treating a bacterial infection in a host comprising:
administering to the host the antibiotic product of claim 14 once-a-day.

48. A process for treating a bacterial infection in a host comprising:
administering to the host the antibiotic product of claim 15 once-a-day.

49. A process for treating a bacterial infection in a host comprising:
administering to the host the antibiotic product of claim 16 once-a-day.

50. A process for treating a bacterial infection in a host comprising:
administering to the host the antibiotic product of claim 17 once-a-day.

51. A process for treating a bacterial infection in a host comprising:
administering to the host the antibiotic product of claim 18 once-a-day.

52. A process for treating a bacterial infection in a host comprising:
  administering to the host the antibiotic product of claim 19 once-a-day.

53. A process for treating a bacterial infection in a host comprising:
  administering to the host the antibiotic product of claim 20 once-a-day.

54. A process for treating a bacterial infection in a host comprising:
  administering to the host the antibiotic product of claim 21 once-a-day.

55. A process for treating a bacterial infection in a host comprising:
  administering to the host the antibiotic product of claim 22 once-a-day.

56. A process for treating a bacterial infection in a host comprising:
  administering to the host the antibiotic product of claim 23 once-a-day.

57. A process for treating a bacterial infection in a host comprising:
  administering to the host the antibiotic product of claim 24 once-a-day.

58. A process for treating a bacterial infection in a host comprising:
  administering to the host the antibiotic product of claim 25 once-a-day.

59. A process for treating a bacterial infection in a host comprising:
  administering to the host the antibiotic product of claim 26 once-a-day.

60. A process for treating a bacterial infection in a host comprising:
  administering to the host the antibiotic product of claim 27 once-a-day.

61. A process for treating a bacterial infection in a host comprising:
  administering to the host the antibiotic product of claim 28 once-a-day.

62. A process for treating a bacterial infection in a host comprising:
  administering to the host the antibiotic product of claim 29 once-a-day.

63. A process for treating a bacterial infection in a host comprising:
  administering to the host the antibiotic product of claim 30 once-a-day.

64. A process for treating a bacterial infection in a host comprising:
  administering to the host the antibiotic product of claim 31 once-a-day.

65. A process for treating a bacterial infection in a host comprising:
  administering to the host the antibiotic product of claim 32 once-a-day.

66. A process for treating a bacterial infection in a host comprising:
  administering to the host the antibiotic product of claim 33 once-a-day.

* * * * *

UNITED STATES PATENT AND TRADEMARK OFFICE
CERTIFICATE OF CORRECTION

PATENT NO. : 6,610,328 B2
DATED : August 26, 2003
INVENTOR(S) : Rudnic et al.

It is certified that error appears in the above-identified patent and that said Letters Patent is hereby corrected as shown below:

Title page,
Item [63], Related U.S. Application Data, after "Feb. 23," and before "." delete "2000" and insert -- 2001 --

Column 1,
Line 5, after "Feb. 23," and before "which" delete "2000," and insert -- 2001, --

Column 7,
Line 29, after "hydroxychitosan," and before ", cross-linked" delete "hydroxymethylatedchito san" and insert -- hydroxymethylatedchitosan --

Column 15,
Line 63, before "® L 30 D-55" delete "Eudragite" and insert -- Eudragit --

Column 17,
Line 30, after "PH" and before "using" delete "1O 1" and insert -- 101 --

Column 19,
Line 25, after "pellets" and before "the" delete "containe" and insert -- contain --
Line 64, after "at" and before "using" delete "600º C." and insert -- 60º C --

Column 20,
Line 13, after "Eudragit ® L 30" and before "/Eugragit NE" delete "D-S55" and insert -- D-55 --

Column 24,
Line 29, after "stirring" and before "until" delete "and completely"

Column 25,
Line 6, after "FS" and before "54.8" delete "300" and insert -- 30D --

UNITED STATES PATENT AND TRADEMARK OFFICE
CERTIFICATE OF CORRECTION

PATENT NO. : 6,610,328 B2
DATED : August 26, 2003
INVENTOR(S) : Rudnic et al.

It is certified that error appears in the above-identified patent and that said Letters Patent is hereby corrected as shown below:

Column 27,
Line 27, after "stirring" and before "until" delete "and completely"
Line 31, before "the talc" delete "dd" and insert -- Add --

Signed and Sealed this

Twenty-seventh Day of July, 2004

JON W. DUDAS
*Acting Director of the United States Patent and Trademark Office*